United States Patent
Hueggenberg et al.

(10) Patent No.: US 11,583,605 B2
(45) Date of Patent: Feb. 21, 2023

(54) METHOD FOR CONTROLLING UNPLEASANT ODORS

(71) Applicant: GreenAirSystems GmbH, Witten (DE)

(72) Inventors: Udo Hueggenberg, Hattingen (DE); Franziska Hueggenberg, Hattingen (DE)

(73) Assignee: GreenAirSystems GmbH, Witten (DE)

(*) Notice: Subject to any disclaimer, the term of this patent is extended or adjusted under 35 U.S.C. 154(b) by 153 days.

(21) Appl. No.: 16/961,363

(22) PCT Filed: Dec. 19, 2018

(86) PCT No.: PCT/EP2018/085827
§ 371 (c)(1),
(2) Date: Jul. 10, 2020

(87) PCT Pub. No.: WO2019/137770
PCT Pub. Date: Jul. 18, 2019

(65) Prior Publication Data
US 2020/0345886 A1 Nov. 5, 2020

(30) Foreign Application Priority Data
Jan. 12, 2018 (EP) .................... 18151451

(51) Int. Cl.
*A61L 9/14* (2006.01)
*A61L 11/00* (2006.01)
*A61L 101/38* (2006.01)
*A61L 101/36* (2006.01)
*A61L 101/34* (2006.01)

(52) U.S. Cl.
CPC .......... *A61L 9/14* (2013.01); *A61L 11/00* (2013.01); *A61L 2101/34* (2020.08); *A61L 2101/36* (2020.08); *A61L 2101/38* (2020.08); *A61L 2209/134* (2013.01)

(58) Field of Classification Search
CPC ........ A61L 9/14; A61L 11/00; A61L 2101/34; A61L 2101/36; A61L 2101/38; A61L 2209/134; A61L 2209/21; A61L 9/01
See application file for complete search history.

(56) References Cited

U.S. PATENT DOCUMENTS

| | | | | |
|---|---|---|---|---|
| 2010/0193599 | A1* | 8/2010 | Butler | B65D 83/70 239/71 |
| 2014/0162932 | A1* | 6/2014 | Hatakeyama | C11B 9/00 512/2 |
| 2018/0066206 | A1* | 3/2018 | Horenziak | A61L 9/14 |

FOREIGN PATENT DOCUMENTS

| | | | |
|---|---|---|---|
| DE | 100 38 063 A1 | 2/2002 | |
| EP | 2 383 398 B1 | 8/2015 | |
| FR | 3019048 A1 | 10/2015 | |
| JP | 2016-202557 A | 12/2016 | |
| JP | 20160202557 A * | 12/2016 | .............. A61L 9/01 |
| WO | 02/13776 A2 | 2/2002 | |

OTHER PUBLICATIONS

International Search Report in PCT/EP2018/085827, dated Jun. 26, 2019.

* cited by examiner

*Primary Examiner* — Sean E Conley
*Assistant Examiner* — Brendan A Hensel
(74) *Attorney, Agent, or Firm* — Collard & Roe, P.C.

(57) ABSTRACT

In a method for controlling unpleasant odors in discharge air from containers, rooms or plants in which strong smelling substances such as feces, waste or highly odorous foods are stored or processed, a fluid is introduced into the discharge air in a finely distributed form, which physically and/or chemically neutralizes the odor of the substances contained in the discharge air. The fluid is a 0.1% to 8% aqueous solution of an active substance concentrate which is 55-65 wt.-% triethylcitrate, 17.5 to 22.5 wt.-% 1,2 propanediol and 17.5 to 22 wt.-% di-propylene glycol-methylether. Alternatively, the fluid can also be a mixture of a suitable propellant gas mixture and the active substance concentrate specified above.

3 Claims, No Drawings

METHOD FOR CONTROLLING UNPLEASANT ODORS

CROSS REFERENCE TO RELATED APPLICATIONS

This application is the National Stage of PCT/EP2018/085827 filed on Dec. 19, 2018, which claims priority under 35 U.S.C. §119 of European Application No. 18151451.4 filed on Jan. 12, 2018, the disclosure of which is incorporated by reference. The international application under PCT article 21(2) was not published in English.

The invention relates to a method for controlling foul odors in the outgoing air from containers, rooms or plants in which strongly smelling substances such as fecal matter, wastes or strongly smelling foods are kept or processed, by introducing into the outgoing air a fluid in finely divided form which physically and/or chemically neutralizes the odor of the substances present in the outgoing air.

A method of this type is known e.g. from DE 100 38 063 A1. In this known method, the fluid that is sprayed in finely divided form, in this case water, contains as active ingredient admixtures in the form of surfactants and/or surfactant mixtures, enzymes and/or enzyme mixtures, hydrogen peroxide, solutions of oxidizing agents, solutions of reducing agents or amphoteric substances, without the active ingredients that are specifically used here being stated more precisely.

According to the prior art (cf. WO02/13776A2; JP2016/202557; FR 3019 048 A1 and US 2014/162932A1) it is also known in principle to use a fluid that contains triethyl citrate, 1,5-propanediol and dipropylene glycol methyl ether for controlling foul odors on the human body or in rooms inhabited by humans. In the prior art, however, these substances are always employed in conjunction with other active ingredients, such as e.g. perfumes, in order not only to control negative odors but also to create a positive odor by covering and masking.

A further method of the above-mentioned type, but in this case with a precise statement of the active ingredients in detail, is known from the European patent EP 2 383 398 B1, which stems from the same inventors as the present patent application. In this method that is known according to the prior art, the sprayed fluid consists of an aqueous solution containing 2.5 vol. % to 10 vol. % glycerol, 0-2.5 vol. % glycol and 0-2.5 vol. % n-butyl acetate as active ingredients.

Although the method that is operated with this fluid is well established in practice, it nevertheless leaves something to be desired with respect to its efficacy and to the relatively large minimum quantity of active ingredient (glycerol) in the fluid, in particular when it is a matter of eliminating particularly strongly smelling foul odors. This disadvantage is particularly significant when extremely large quantities of outgoing air have to be treated, for example the outgoing air from plants located in large halls or even in the open air, such as e.g. plants for sorting waste, plants for mixing asphalt, biogas plants, open effluent channels or clarifiers.

It is therefore an object of the present invention to improve the method of the above-mentioned type with respect to its efficacy and at the same time to reduce considerably the quantity of active ingredients required.

To achieve this object, starting from the method of the above-mentioned type, the invention proposes that the fluid is a 0.1% strength to 8% strength aqueous solution of an active ingredient concentrate, which consists to an extent of 55-65 wt. % of triethyl citrate, 17.5-22.5 wt.% of 1,2-propanediol and 17.5-22.5 wt. % of dipropylene glycol methyl ether.

Surprisingly, it has been found that when such an active ingredient concentrate is used, the quantity of active ingredient in the aqueous fluid can be reduced considerably without having a negative impact on the odor-eliminating effect and without the need for further active ingredients. The significantly higher suppression or absorption of the odor is attributable to the interaction between the main component triethyl citrate, which has an extracting and catalytic action, the mist-forming and hygroscopic 1,2-propanediol, and dipropylene glycol methyl ether which acts as a solvent and is likewise hygroscopic. The catalytic action of triethyl citrate in particular has the effect that odors are not just covered or masked but are eliminated by chemical reaction of the odor-forming substances. These odor-forming substances are in particular polycyclic aromatic hydrocarbons (PAHs) with condensed ring systems, which are broken by the above-mentioned actions of triethyl citrate and, as a result, not only lose their odor effect for the most part but are also rendered rapidly degradable by natural degradation processes.

However, the positive effects of the new active ingredient combination explained above can be achieved not only when the active ingredient concentrate is used in diluted form in an aqueous solution but can also be achieved when the active ingredient concentrate is introduced into the foul-smelling air in a sufficiently finely divided form in another manner. In particular, it is quite possible to ensure a sufficiently fine division of the active ingredients by mixing the concentrate in an appropriate quantity with a suitable propellant gas and spraying it from a suitable spray can with the aid of this propellant gas. This possibility is suitable in particular when the foul odor of small quantities of air has to be controlled.

The present invention thus further provides a method for controlling foul odors in the air of rooms in which strongly smelling substances such as fecal matter, wastes or strongly smelling foods are kept or processed, by introducing into the room air a fluid in finely divided form which physically and or chemically neutralizes the odor of the substances present in the room air, this method being characterized in that the fluid is a mixture of a propellant gas mixture and an active ingredient concentrate which is present at 0.1-8 wt. % in the propellant gas mixture, where the propellant gas mixture consists to an extent of 55-80 wt. % of butane, 15-40 wt. % of propane and 1-25 wt. % of isobutane, and the active ingredient concentrate consists to an extent of 55-65 wt. % of triethyl citrate, 17.5-22.5 wt. % of 1,2-propanediol and 17.5-25.5 wt. % of dipropylene glycol methyl ether.

The following tests for controlling foul odors with the methods according to the invention were extraordinarily successful:

EXAMPLE 1

In the hall of a waste sorting plant for light packaging waste (LPW sorting plant), a finely divided mist consisting of 2.5 wt. % triethyl citrate, 1.25 wt. % propanediol, 1.25 wt. % dipropylene glycol methyl ether and 95 wt. % water was sprayed using fans and dual nozzles. This measure enabled the foul odors to be eliminated down to the perception threshold. The spraying devices here were arranged in a targeted manner in the region of the hall doors, which had to remain open continuously because of the constant traffic. As a result of this targeted arrangement of the odor elimination arrangement in the region of the hall doors, an effective odor barrier was achieved so that nearby residents were no longer disturbed by the foul odors from this LPW sorting plant

EXAMPLE 2

In the region of a largely open-air loading facility for asphalt at an asphalt mixing plant, spraying devices were installed in the region of the loading flaps, by which a fine mist consisting of 1 wt. % triethyl citrate, 0.5 wt. % propanediol, 0.5 wt. % dipropylene glycol methyl ether and 98 wt. % water was sprayed into the exhaust air that formed during the loading operation. Despite the very low content of active ingredient in the fluid here, this measure enabled almost complete elimination of the asphalt odor to be achieved.

EXAMPLE 3

In households with domestic pets, to eliminate foul odors, spray cans were employed from which a mixture of propellant gas and active ingredient concentrate according to the invention was sprayed in finely divided form into the air of the odorous rooms. Here too, almost complete elimination of the foul odors was obtained.

The invention claimed is:

1. A method for controlling foul odors in exhaust air from containers, rooms or plants in which a substance having an odor is kept or processed, by introducing an active ingredient in finely divided form into the exhaust air, which physically and/or chemically neutralizes the odor of the substance present in the exhaust air, wherein the active ingredient is a concentrate which consists of 55-65 wt % of triethyl citrate, 17.5-22.5 wt % of 1,2-propanediol and 17.5-22.5 wt % of di-propylene glycol methyl ether.

2. The method according to claim 1, wherein the active ingredient concentrate is diluted with water to a 0.1% to 8% aqueous solution and is sprayed into the exhaust air as a finely divided mist.

3. The method according to claim 1, wherein 0.1 to 8 wt % of the active ingredient concentrate is introduced into a propellant gas mixture, which comprises 55-80 wt % of butane, 15-40 wt % of propane and 1-25 wt % of isobutane, and is sprayed with the help of this propellant mixture into the outgoing air.

* * * * *